United States Patent
Patel et al.

(10) Patent No.: US 7,459,565 B2
(45) Date of Patent: Dec. 2, 2008

(54) REGIOSPECIFIC PROCESS FOR THE PREPARATION OF 4-[1-(4-CYANOPHENYL)-1-(1,2,4-TRIAZOL-1-YL)METHYL] BENZONITRILE

(75) Inventors: Hetalkumar Virendrabhai Patel, Akota (IN); Raja Jyotir Jani, Akota (IN); Rajamannar Thennati, Akota (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 484 days.

(21) Appl. No.: 10/544,460

(22) PCT Filed: Feb. 5, 2004

(86) PCT No.: PCT/IN2004/000036

§ 371 (c)(1),
(2), (4) Date: Aug. 4, 2005

(87) PCT Pub. No.: WO2004/076409

PCT Pub. Date: Sep. 10, 2004

(65) Prior Publication Data

US 2006/0128775 A1 Jun. 15, 2006

(30) Foreign Application Priority Data

Feb. 6, 2003 (IN) .................. 167/MUM/2003

(51) Int. Cl.
*C07D 249/00* (2006.01)
(52) U.S. Cl. ..................................... 548/262.2
(58) Field of Classification Search ............... 548/262.2
See application file for complete search history.

(56) References Cited

U.S. PATENT DOCUMENTS 4,978,672 A * 12/1990 Bowman et al. ............ 514/383
5,473,078 A * 12/1995 Bowman et al. ......... 548/262.2
5,567,819 A    10/1996 Houghton

* cited by examiner

*Primary Examiner*—Joseph K. McKane
*Assistant Examiner*—Susannah Chung
(74) *Attorney, Agent, or Firm*—Banner & Witcoff, Ltd.

(57) ABSTRACT

A regiospecific process for the preparation of 4-[1-(4-cyanophenyl)-1-(1,2,4-triazol-1-yl)methyl]benzonitrile comprising reacting 4-halomethylbenzonitrile with 4-amino-1,2,4-triazole followed by deamination and reaction with 4-fluorobenzonitrile.

12 Claims, No Drawings

REGIOSPECIFIC PROCESS FOR THE PREPARATION OF 4-[1-(4-CYANOPHENYL)-1-(1,2,4-TRIAZOL-1-YL)METHYL] BENZONITRILE

FIELD OF THE INVENTION

The present invention relates to a regiospecific process for the preparation of 4-[1-(4-cyanophenyl)-1-(1,2,4-triazol-1-yl)methyl]benzonitrile, a compound of formula 1, free of isomeric and triaryl impurities. 4-[1-(4-cyanophenyl)-1-(1,2,4-triazol -1-yl)methyl]benzonitrile or Letrozole (INN name) is an antineoplastic agent.

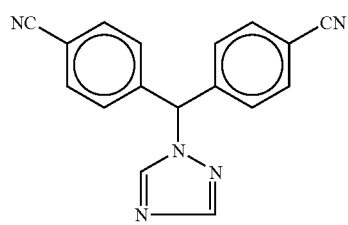

Formula 1

BACKGROUND OF THE INVENTION

U.S. Pat. No. 4,978,672 (referred to herein as '672, Indian Reference not available) provides 4-[alpha-(4-cyanophenyl)-1-(1,2,4-triazolyl)-methyl]benzonitrile and the process of its preparation. The patent discloses reacting 4-bromomethyl-benzonitrile with 1,2,4-triazole to yield 4-[1-(1,2,4-triazol-1-yl)methyl]benzonitrile. 4-[1-(1,2,4-triazol-1-yl)methyl]benzonitrile is then reacted with 4-fluorobenzonitrile to give 4-[1-(4-cyanophenyl)-1-(1,2,4-triazol-1-yl)methyl]benzonitrile. This patent does not disclose the purity of 4-[1-(4-cyanophenyl)-1-(1,2,4-triazol-1-yl)methyl]benzonitrile, compound of formula 1. When we followed the patented process we also get the unwanted isomer 4-[1-(1,2,4-triazol-4-yl)methyl]benzonitrile, a compound of formula 4 (20 to 40%) in step 1. When the reaction mixture of step 1 is treated with 4-fluorobenzonitrile it yields 4-[1-(4-cyanophenyl)-1-(1,2,4-triazol-1-yl)-methyl]-benzonitrile, a compound of formula 1, and its isomer, a compound of formula 5. Thus the impurity of formula 4 has to be separated before treating it with 4-fluorobenzonitrile, which involves an additional step of column purification, which is reported in '672 and makes the process tedious and commercially unviable.

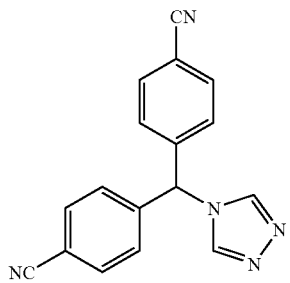

Formula 5

Further, if the intermediate contains an impurity like 4-toluonitrile or other related impurities, that are present in the raw material viz. 4-(bromomethyl)benzonitrile, in step 2, the impurities would participate in the reaction with 4- fluorobenzonitrile leading to the formation of 4-[1,1-Bis(4-cyanophenyl)methyl]benzonitrile (referred to herein as 'tris impurity') compound of formula 6 and other side products.

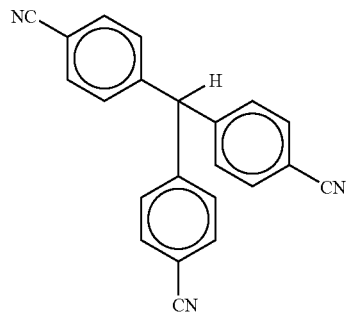

Formula 6

OBJECTS OF THE INVENTION

The object of the present invention is to provide a regiospecific process for the preparation of 4-[1-(4-cyanophenyl)-1-(1,2,4-triazol-1-yl) methyl]benzonitrile, a compound of formula 1, free of impurities viz. 4-[1-(4-cyanophenyl)-1-(1,2,4-triazol-4-yl)methyl]benzonitrile, compound of formula 5, and 4-[1,1-Bis(4-cyanophenyl)methyl]benzonitrile compound of formula 6.

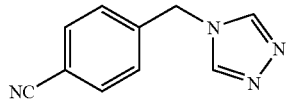

Formula 4

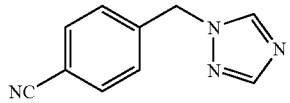

Formula 3

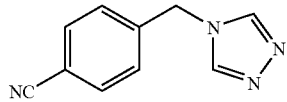

Formula 4

Another object of the present invention is to provide a regiospecific process for the preparation of 4-[1-(1H-1,2,4-triazol-1-yl)methylene]benzonitrile, a compound of formula 3, substantially free of compound of formula 4 by eliminating the formation of an unwanted isomer.

Yet another object of the present invention is to purify the intermediate compound of formula 2, which is a precursor to the regioselective isomer using simple purification technique, in order to eliminate all the impurities, which would be present in its raw material and yield compound of formula 1 free of also the 'tris impurity' compound of formula 6.

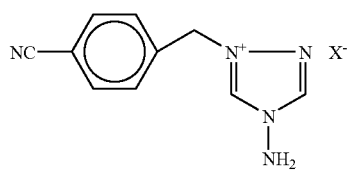

Formula 2

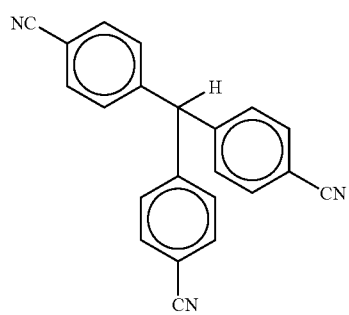

Formula 6

SUMMARY OF THE INVENTION

The regiospecific process for preparation of 4-[1-(4-cyanophenyl)-1-1,2,4-triazol-1-yl)methyl]benzonitrile, a compound of formula 1, said process comprising

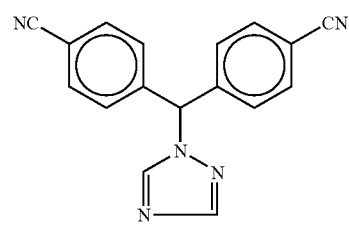

formula 1

(a) reacting 4-halomethylbenzonitrile with 4-amino-1,2,4-triazole to give 4-[(4-amino-4H-1,2,4-triazolium-1-yl)methyl]benzonitrile halide, a compound of formula 2;

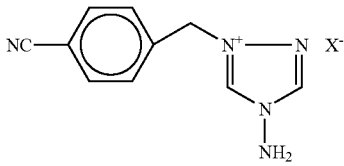

Formula 2

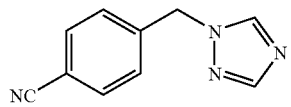

Formula 3

(b) deaminating the compound of formula 2 to 4-[1-(1H-1,2,4-triazol-1-yl)methylene]benzonitrile, a compound of formula 3; and (c) reacting the compound of formula 3 with 4-fluorobenzonitrile.

The present invention also provides a regiospecific process for the preparation of compounds of formulae 2 and 3 and simple purification of compound of formula 2.

DETAILED DESCRIPTION OF THE INVENTION

The present invention provides a regiospecific process for the preparation of 4-[1-(4-cyanophenyl)-1-(1,2,4-triazol-1-yl)methyl]benzonitrile, a compound of formula 1, substantially free of impurities starting with 4-amino-1,2,4-triazole in which the possibility of 4-alkylation is blocked by an amino group. This eliminates the formation of the unwanted impurity 4-[1-(1,2,4-triazol-4-yl)methyl]benzonitrile, a compound of formula 4, which leads to the impurity, a compound of formula 5, in the final stage preparation of 4-[1-(4-cyanophenyl)-1-(1,2,4-triazol-1-yl)methyl]benzonitrile, compound of formula 1.

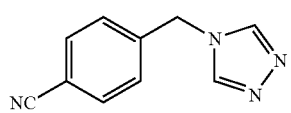

Formula 4

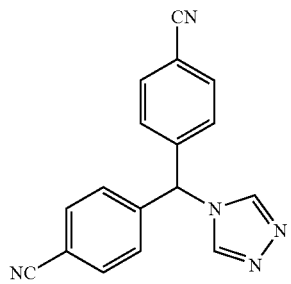

Formula 5

The process of the present invention provides 4-[1-(4-cyanophenyl)-1-(1,2,4-triazol-1-yl)methyl]benzonitrile, a compound of formula 1, substantially free of impurities. The impurities may be 4-[1-(4-cyanophenyl)-1-(1,2,4-triazol-4-yl)methyl]benzonitrile, compound of formula 5, and/or 4-[1,1-Bis(4-cyanophenyl)methyl]benzonitrile, compound of formula 6.

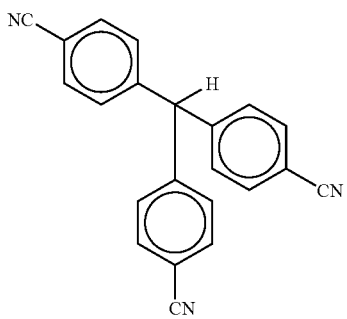

Formula 6

4-[1-(4-cyanophenyl)-1-(1,2,4-triazol-1-yl)methyl]benzonitrile, compound of formula 1, provided by the process of this invention has purity greater than 99.5%, preferably greater than 99.8%.

The regiospecific process of the present invention is carried out in 3 steps by reacting 4-halomethylbenzonitrile with 4-amino-1,2,4-triazole to obtain 4-[(4-amino-1,2,4-triazolium-1-yl)methyl]benzonitrile halide, a compound of formula 2, deaminating to obtain 4-[1-(1,2,4-triazol-1-yl)methyl]benzonitrile, a compound of formula 3, and reacting the compound of formula 3 with 4-fluorobenzonitrile to yield 4-[1-(4-cyanophenyl)-1-(1,2,4-triazol-1-yl)methyl]benzonitrile, a compound of formula 1, substantially free of impurities.

According to one embodiment of the process of the present invention step (a) of the process is carried out by reacting 4-halomethylbenzonitrile with 4-amino-1,2,-triazole by heating in a solvent selected from water, alcohols selected from alkyl, aryl or alkylaryl alcohols like ethanol, methanol, n-propanol, isopropanol, n-butanol, isobutanol, benzyl alcohol and the like; ketones selected from alkyl, aryl or alkylaryl ketones such as acetone, methylisobutyl ketone, methylethyl ketone, acetophenone; nitrites such as benzonitrile, acetonitrile; and dimethylsulphoxide, diphenylether, dimethylformamide, dichlorobenzene and the like.

4-halomethylbenzonitrile may be selected from 4-chloromethylbenzonitrile, 4-iodomethylbenzonitrile and 4-bromomethylbenzonitrile, the preferred being 4-bromomethylbenzonitrile.

According to the preferred process of the present invention step (a) of the process may be carried out in an alcoholic solvent like isopropanol.

The process of the present invention step (a) is carried out at temperatures ranging from about 20 to 150° C., preferably about 75 to 100° C., the most preferred being about 80 to 85° C.

The process of the present invention step (a) is carried out for about 3 to 8 hours, preferably about 4 to 6 hours, the most preferred being about 5 hours.

The reaction mixture on completion of the reaction is cooled and filtered. The compound of formula 2 obtained may be purified by standard techniques known to those skilled in this art for instance, simple leaching with solvents like ketones, nitrites, esters, ethers, preferably alcohols and alkanes, most preferred being isopropanol and hexane to give pure compound of formula 2.

According to another embodiment of the process of the present invention step (b) is carried out by deaminating compound of formula 2 using any deaminating agent like (i) nitrites which may be selected from inorganic nitrites of sodium or potassium, and organic nitrites such as alkyl nitrites, preferably sodium nitrite is used; or (ii) nitrous acid. The preferred deaminating agent being nitrous acid. Nitrous acid may be prepared insitu by reacting inorganic nitrite with mineral acid.

In the preferred process of the present invention step (b) is carried out by deaminating compound of formula 2 with sodium nitrite in the presence of mineral acid like hydrochloric acid under cold conditions about 0 to 5° C. over a period of about 6 to 8 hours.

The reaction mixture may be worked up by standard techniques known to those skilled in this art. For instance, the unreacted nitrous acid is decomposed with urea at the end of the reaction and impurities removed by extraction with a solvent selected from halo substituted or unsubstituted alkyl and aryl hydrocarbons such as hexane, toluene, xylenes, methylene chloride, chlorobenzene and the like, alkyl or aryl ketones like methylisobutyl ketone, and the like, preferably dichloromethane.

The aqueous solution is adjusted to pH>8 with a base. Preferable base being an aqueous ammonical solution.

After adjusting the pH compound of formula 3 is extracted with a solvent selected from halo substituted or unsubstituted alkyl and aryl hydrocarbons such as hexane, toluene, xylenes, methylene chloride, chlorobenzene and the like, alkyl or aryl ketones like acetone, methylisobutyl ketone, and the like, preferably dichloromethane. The organic layer containing the compound of formula 3 is washed with water and then concentrated by heating and/or applying vacuum to give a syrupy liquid. The syrupy liquid is then converted to a solid by adding a solvent mixture of two or more solvents selected from halo substituted or unsubstituted alkyl and aryl hydrocarbons such as hexane, toluene, xylenes, methylene chloride, chlorobenzene and the like, alkyl or aryl ketones like acetone, methylisobutyl ketone, methylethyl ketone and the like, alky or aryl alcohols like ethanol, methanol, isopropanol, benzyl alcohol and the like, alky or aryl nitriles like benzonitrile, acetonitrile and the like, preferably isopropanol and hexane mixture. The volume ratio of isopropanol to hexane may vary from 10:90 to 90:10, preferably 50:50, the most preferred being 20:80.

The solution containing the solids is cooled to below 25° C., preferably 8-10° C., stirred, filtered and washed with an aprotic solvent selected from aliphatic hydrocarbons, aromatic hydrocarbons and the like, most preferably hexane to yield a compound of formula 3.

The compound of formula 3 obtained by the process of the present invention is free of its isomer, compound of formula 4.

According to yet another embodiment of the process of the present invention step (c) is carried out by treating the compound of formula 3 with 4-fluorobenzonitrile to yield 4-[1-(4-cyanophenyl)-1-(1,2,4-triazol-1-yl)methyl]benzonitrile, a compound of formula 1, substantially free of impurities in an organic solvent such as dimethylformamide in the presence of a base such as potassium tertiary butoxide at lower temperatures such as −5 to −10° C.

The reaction mixture is worked up by standard techniques known to those skilled in this art. For instance, at the end of the reaction the reaction mixture is worked up by extracting with an organic solvent, concentrating, and optionally purifying to yield 4-[1-(4-cyanophenyl)-1-(1,2,4-triazol-1-yl)methyl]benzonitrile,a compound of formula 1, substantially free of impurities. The purifying methods may be selected from washing, extracting, suspending, precipitating, leaching, recrystallizing and the like. Preferably, recrystallization of compound of formula 1 with a solvent selected from polar and non-polar solvents such as alcohols, ketones and esters, preferably esters, the preferred being ethyl acetate.

Methods of preparing 4-[1-(4-cyanophenyl)-1-(1,2,4-triazol-1-yl)methyl]benzonitrile are disclosed in U.S. Pat. No. 4,978,672 (Indian Reference not available).

The invention is illustrated but not restricted by the description in the following example.

EXAMPLES

Example 1

(a) Preparation of 4-[(4-amino-1,2,4-triazolium-1-yl)methyl] benzonitrile bromide, compound of formula 2:

4-bromomethylbenzonitrile (300.0 gm, 1.530 moles) was heated with 4-amino-1,2,4-triazole (141.5 gm, 1.683 moles) in isopropanol (3.0 L) as a solvent for 5.0 hours at 80°-85° C. temperature. Reaction mixture was cooled gradually to room temperature and further to 0°-5° C. temperature and stirred for 2.0 hrs and filtered.

(b) Purification of 4-[(4-amino-1,2,4-triazolium-1-yl)methyl]benzonitrile bromide, compound of formula 2:

The filtered solid was washed with isopropanol (300.0 ml) followed by hexane (300.0 ml), gave 4-[(4-amino-1,2,4-triazolium-1-yl)methyl] benzonitrile bromide, compound of formula 2. (310.0 gm, 72.2% yield).

(c) Preparation of 4-11-(1,2,4-triazol-1-yl)methyll benzonitrile, compound of formula 3:

4-[(4-amino-1,2,4-triazolium-1-yl)methyl]benzonitrile bromide (275.0 gm, 0.982 moles) was dissolved in water (1.1 L) and cooled to 0°-5° C. temperature. To this solution, was added hydrochloric acid (196.5 ml, 1.963 moles) at 0°-5° C. temperature followed by solution of sodium nitrite (74.5 gm, 1.080 moles) in water (275.0 Ml) at 0°-5° C. temperature within 6.0 hrs, followed by stirring at 30°-35° C. temperature for 2.0-3.0 hrs. After reaction was over, unreacted nitrous acid was decomposed with urea, extracted with dichloromethane to remove impurities. Finally, aqueous layer was basified to pH 8.0-8.5 by adding 25% ammonia solution and product was extracted with dichloromethane An organic layer containing product was washed with water and concentrated to give syrupy liquid, to which was added isopropanol:hexane (20:80), slurry so obtained was cooled to 8-10° C. temperature, stirred for 2.0 hrs, filtered and washed with hexane (75.0 ml) to give 4-[1-(1,2,4-triazolyl)methyl]benzonitrile,compound of formula 3 free of compound of formula 4. (150.0 gm, 82.9% yield)

(d) Preparation of 4-[1-(4-cyanophenyl)-1-(1,2,4triazol-1-yl) methyl]benzonitrile, compound of formula 1:

The solution of 4-[1-(1,2,4-triazolyl)methyl]benzonitrile (100 gm, 0.543 moles) in N,N-dimethylformamide (500 ml) was added at −10° to −5° C. temperature to the solution of potassium tertiary butoxide (122 gm, 1.085 moles) in N,N-dimethylformamide (750 ml) and stirred for 1.0 hour. To this solution, was added a solution of 4-fluorobenzonitrile (77 gm, 0.592 moles) in N,N-dimethylformamide (500 ml) at −10° to −5° C. temperature and stirred for 3.0 hours. Reaction mixture was then neutralized to pH 7.5-8.0 by adding 1.0 N hydrochloric acid (700 ml) and concentrated to remove N,N-dimethylformamide under vacuum. To the residue was added water and product was extracted with ethyl acetate. An organic layer was washed with water and concentrated under vacuum. To the residue was added, isopropyl alcohol, stirred for 1.0 hour and filtered the crude product (125.0 gm). Crude product was recrystallized from hot ethyl acetate (1.37 L) to give 4-[1-(4-cyanophenyl)-1-(1,2,4-triazol-1-yl)methyl]benzonitrile, compound of formula 1. (90 g, 58 % yield, 99.90% HPLC purity).

We claim:

1. A regiospecific process for preparation of 4-[1-(4-cyanophenyl)-1-(1,2,4-triazol-1-yl)methyl]benzonitrile, a compound of formula 1,

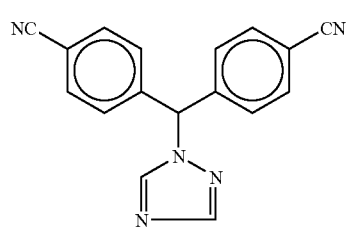

Formula 1 said process comprising:

(a) reacting 4-halomethylbenzonitrile with 4-amino-1,2,4-triazole to give 4-[(4-amino-4H-1,2,4-triazolium-1-yl)methyl]benzonitrile halide, a compound of formula 2,

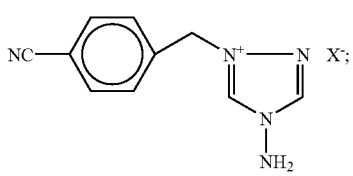

Formula 2 deaminating the compound of formula 2 to 4-[1-(1H-1,2,4-triazol-1-yl)methylene]benzonitrile, a compound of formula 3,

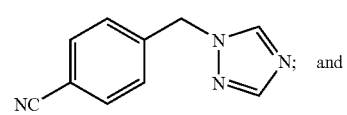

Formula 3

(c) reacting the compound of formula 3 with 4-fluorobenzonitrile.

2. A process as claimed in claim 1 wherein in step (a) the 4-halomethyl-benzonitrile is 4-bromomethylbenzonitrile.

3. A process as claimed in claim 1 wherein step (a) is carried out in the presence of a solvent selected from an alcohol.

4. A process as claimed in claim 3 wherein the alcohol is isopropanol.

5. A process as claimed in claim 1 wherein step (a) is carried out at a temperature from about 20 to 150° C. for about 3 to 8 hours.

6. A process as claimed in claim 1 wherein compound of formula 2 is further purified by leaching the product of step (a) with an organic solvent(s) selected from ketones, nitrites, esters, ethers, alcohols and alkanes or mixtures thereof.

7. A process as claimed in claim 1 wherein step (b) is carried out by deaminating the compound of formula 2 to 4-[1-(1H-1,2,4-triazol-1-yl)methylene]benzonitrile, a compound of formula 3 with nitrous acid generated in situ with an inorganic nitrite and a mineral acid.

8. A process as claimed in claim 7 wherein the compound of formula 3 is free of its isomer, compound of formula 4;

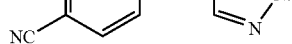

Formula 4

9. A process as claimed in claim 1 further comprising purification of the compound of formula 1 wherein the said purification maybe selected from the group consisting of washing, extracting, suspending, precipitating, leaching and recrystallizing.

10. A process as claimed in claim 9 wherein the compound of formula 1 is purified by recrystallizing from ethyl acetate.

11. A process as claimed in claim 9 wherein 4-[1-(4-cyanophenyl)-1-(1,2,4-triazol-1-yl)methyl]benzonitrile has purity greater than 99.5%.

12. A process as claimed in claim 9 wherein 4-[1-(4-cyanophenyl)-1-(1,2,4-triazol-1-yl)methyl]benzonitrile is free from the impurities compounds of formulae 5 and 6;

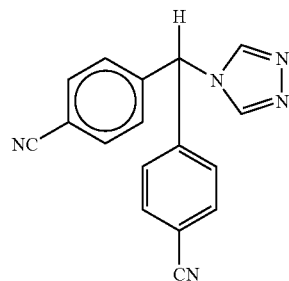

Formula 5

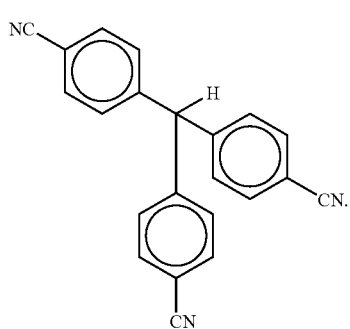

Formula 6

* * * * *